United States Patent
Ouchi

(10) Patent No.: US 6,328,731 B1
(45) Date of Patent: Dec. 11, 2001

(54) TREATING INSTRUMENT FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/411,160

(22) Filed: Oct. 1, 1999

(30) Foreign Application Priority Data

Oct. 9, 1998 (JP) .................................................. 10-287391

(51) Int. Cl.[7] .......................................................... A61B 1/00
(52) U.S. Cl. .............................. 606/1; 600/121; 600/139; 600/144; 604/525
(58) Field of Search ............................... 606/1; 600/121, 600/125, 159, 139, 136, 144; 604/525, 533, 534, 535

(56) References Cited

U.S. PATENT DOCUMENTS

| | | | |
|---|---|---|---|
| 5,358,493 | * 10/1994 | Scheeich, Jr. et al. | 604/264 |
| 5,409,455 | * 4/1995 | Belden | 604/43 |
| 5,489,275 | * 2/1996 | Thomson et al. | 604/264 |
| 5,531,719 | * 7/1996 | Takahashi | 604/280 |
| 6,135,992 | * 10/2000 | Wang | 604/525 |

* cited by examiner

Primary Examiner—Linda C. M. Dvorak
Assistant Examiner—Jocelyn Ram
(74) Attorney, Agent, or Firm—Greenblum & Bernstein P.L.C.

(57) ABSTRACT

A treating instrument for an endoscope has a flexible sheath and an operating part connected to the proximal end of the flexible sheath. A first buckling preventing member formed from a flexible cylindrical material covers a proximal end portion of the flexible sheath. One end of the first buckling preventing member is secured to the operating part. A second buckling preventing member formed from a flexible cylindrical material overlaps the first buckling preventing member at a region extending from an intermediate position on the first buckling preventing member to the proximal end thereof. One end of the second buckling preventing member is secured to the operating part.

10 Claims, 5 Drawing Sheets

TREATING INSTRUMENT FOR ENDOSCOPE

BACKGROUND OF THE INVENTION

The present disclosure relates to subject matter contained in Japanese Patent Application No. 10-287391 (filed on Oct. 9, 1998), which is expressly incorporated herein by reference in its entirety.

1. Field of the Invention

The present invention relates to a treating instrument for an endoscope in which the proximal end of a flexible sheath is connected to an operating part.

2. Description of the Prior Art

As the flexible sheath of a treating instrument for an endoscope, a coil pipe that is formed by close-winding a thin stainless steel wire with a uniform diameter or a tetrafluoroethylene resin tube (Teflon TM tube) is widely used. The proximal end of the flexible sheath is connected to an operating part.

Normally, the flexible sheath does not buckle even if it is bent with a considerably small radius of curvature. However, if the flexible sheath is bent in the vicinity of the joint between the flexible sheath and the operating part, which is a rigid body, the flexible sheath often buckles and breaks easily because of a sharp change in the state of bending.

To prevent the flexible sheath from buckling, the proximal end portion of the flexible sheath is generally covered with a buckling preventing member formed from a tetrafluoroethylene resin tube or a close-wound coil tube, for example.

If the buckling strength (resistance to an external force applied in the bending direction) of the abovedescribed buckling preventing member is set excessively strong, the flexible sheath is likely to buckle at the boundary between the sheath and the buckling preventing member. Therefore, it is preferable to set the buckling strength of the buckling preventing member roughly in the range of from several times to 10 times as high as the buckling strength of the flexible sheath.

However, the sheath of the treating instrument is formed to be highly flexible so as not to damage built-in components of the endoscope, such as an optical fiber bundle, when inserted into or removed from the instrument-inserting channel of the endoscope.

Therefore, if the buckling strength of the buckling preventing member is set at a level just suitable for the flexible sheath, the buckling preventing effect may be insufficient at the joint between the flexible sheath and the operating part. Consequently, buckling breakage is likely to occur.

SUMMARY OF THE INVENTION

An object of the present invention is to provide a treating instrument for an endoscope which is capable of surely preventing buckling breakage of the flexible sheath at the joint between the flexible sheath and the operating part.

Other objects and advantages of the present invention will become apparent from the following detailed description of illustrated embodiments of the invention.

According to the present invention, there is provided a treating instrument for an endoscope having a flexible sheath and an operating part connected to the proximal end of the flexible sheath. The treating instrument includes a first buckling preventing member formed from a flexible cylindrical material and provided to cover a proximal end portion of the flexible sheath. One end of the first buckling preventing member is secured to the operating part. The treating instrument further includes a second buckling preventing member formed from a flexible cylindrical material and provided to overlap the first buckling preventing member at a region extending from an intermediate position on the first buckling preventing member to the proximal end thereof. One end of the second buckling preventing member is secured to the operating part.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
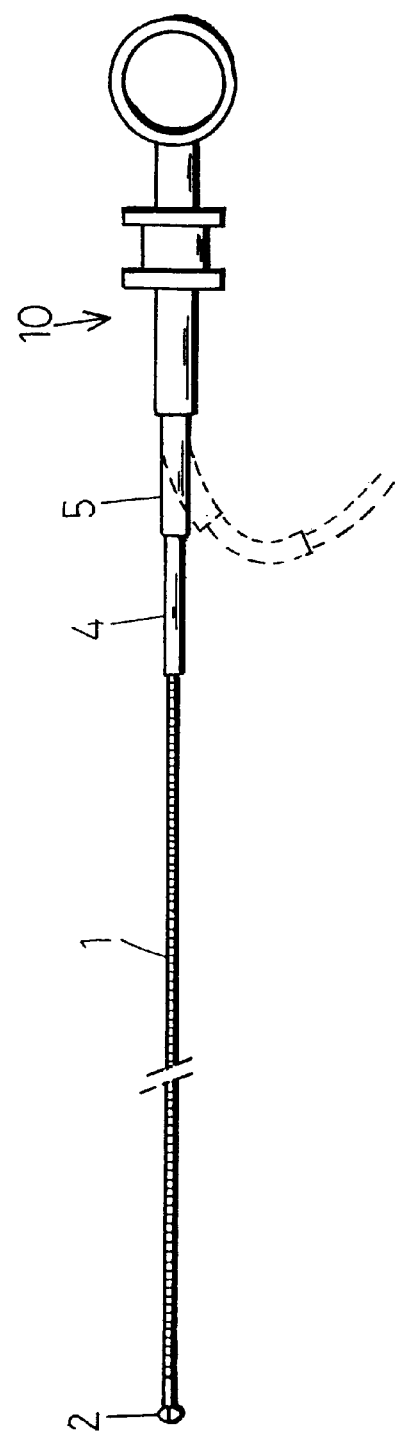
FIG. 1 is a side view of a treating instrument for an endoscope according to a first embodiment of the present invention.

FIG. 1 shows a treating instrument for an endoscope according to a first embodiment of the present invention, in which the present invention is applied to a biopsy forceps.

A flexible sheath 1 is removably inserted into an instrument-inserting channel of an endoscope (not shown). For example, the flexible sheath 1 is formed from a coil pipe that is formed by close-winding a thin stainless steel wire with a uniform diameter.

A pair of treating members 2 are provided at the distal end of the flexible sheath 1. The treating members 2 are a pair of forceps cups that are selectively opened or closed by a link mechanism or the like. A control wire is axially movably inserted in the flexible sheath 1. The control wire is axially advanced or retracted at an operating part 10 connected to the proximal end of the flexible sheath 1. The treating members 2 are driven by axially moving the control wire.

At the joint between the flexible sheath 1 and the operating part 10, first and second buckling preventing members 4 and 5 are provided to cover the proximal end portion of the flexible sheath 1. The first and second buckling preventing members 4 and 5 are formed from flexible tubes made of a material, e.g. tetrafluoroethylene resin, polyethylene, or nylon.

Figure 2:
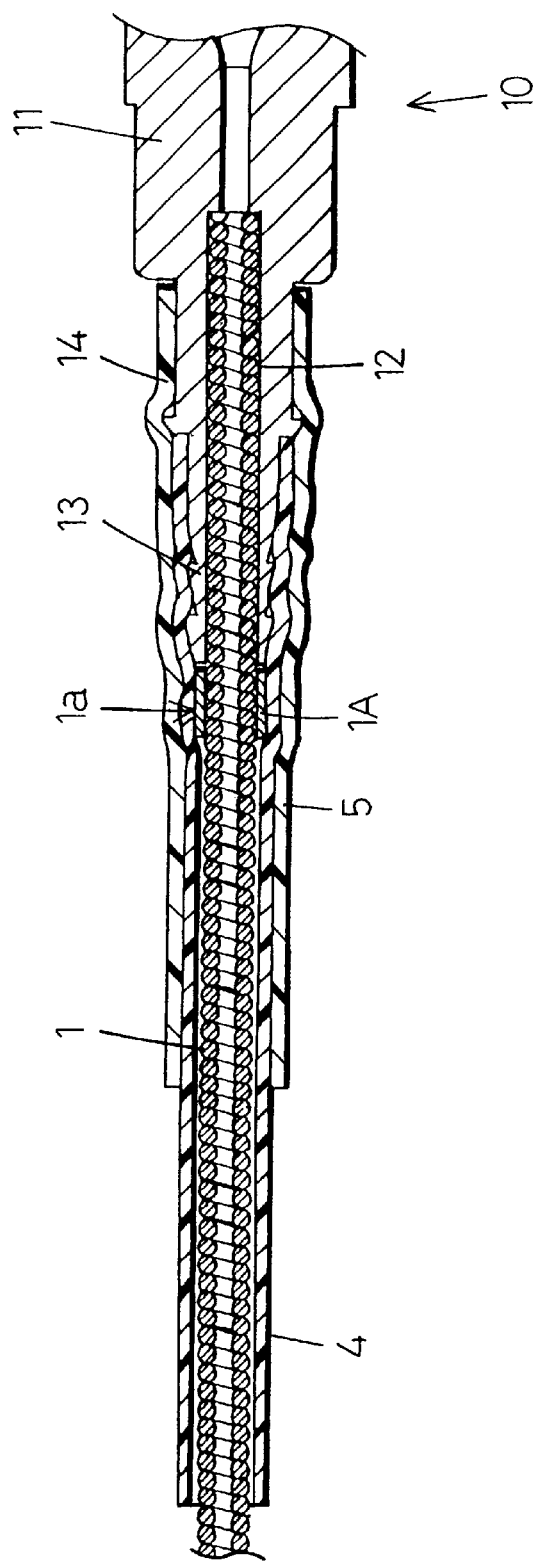
FIG. 2 is a sectional side view of the treating instrument according to the first embodiment of the present invention, showing the joint between a flexible sheath and an operating part and its vicinities.

FIG. 2 shows the joint between the flexible sheath 1 and the operating part 10. In FIG. 2, illustration of the control wire inserted in the flexible sheath 1 is omitted. A short cylindrical member 1A formed from a metal pipe has previously been secured to the outer peripheral surface of a portion of the flexible sheath 1 near the proximal end thereof by bonding or soldering to form a large-diameter portion 1a whereby the outer diameter of the flexible sheath 1 is locally increased.

The proximal end of the flexible sheath 1 is fitted into a sheath inserting hole 12 formed in an end portion of an operating part body 11 constituting the operating part 10. The end portion of the operating part body 11 is formed in the shape of a cylinder coaxial with respect to the sheath-inserting hole 12. A saw-toothed retaining portion 13 and a step portion 14 are formed in series on the outer peripheral surface of the cylindrical end portion of the operating part body 11.

As the proximal end of the flexible sheath 1 is fitted into the sheath-inserting hole 12, the large-diameter portion 1a abuts on the end surface of the operating part body 11. In this state, the proximal end portion of the flexible sheath 1 is covered with the first buckling preventing member 4.

The first buckling preventing member 4 has a uniform wall thickness over the entire length thereof. The inner diameter of the first buckling preventing member 4 is slightly larger than the outer diameter of the flexible sheath 1 but smaller than the outer diameter of the large-diameter portion 1a. The large-diameter portion 1a of the flexible sheath 1 and the saw-toothed retaining portion 13 of the operating part body 11 are forced into the first buckling preventing member 4 from the proximal end of the first buckling preventing member 4.

Consequently, the first buckling preventing member 4 is retained by the saw-toothed retaining portion 13 in such a manner as to press the large-diameter portion 1a of the flexible sheath 1 against the operating part body 11. Thus, the proximal end of the flexible sheath 1 is secured to the operating part body 11.

The second buckling preventing member 5 is formed from a flexible tube of uniform wall thickness that is larger in diameter but shorter in length than the first buckling preventing member 4. The second buckling preventing member 5 has its proximal end portion force-fitted and thus secured to the step portion 14 of the operating part body 11 so as to cover a portion of the first buckling preventing member 4 extending from an intermediate position to the proximal end of the first buckling preventing member 4. Thus, the first buckling preventing member 4 extends forward beyond the distal end of the second buckling preventing member 5.

Accordingly, a proximal end portion of the flexible sheath 1 adjacent to the operating part 10 is covered with a double tube structure formed from the first buckling preventing member 4 and the second buckling preventing member 5, and a portion of the flexible sheath 1 covered with only the first buckling preventing member 4 lies forward of the proximal end portion covered with the double tube structure.

Assuming that the buckling strength of each of the first and second buckling preventing members 4 and 5 is of the order of from 5 to 10 times as high as that of the flexible sheath 1, for example, the proximal end portion of the flexible sheath 1, which is connected to the operating part 10, is first reinforced at a forward end portion thereof with only the first buckling preventing member 4 having a buckling strength about 5 to 10 times as high as that of the flexible sheath 1, and at the portion adjacent to the operating part 10, the flexible sheath 1 is reinforced with the second buckling preventing member 5 in addition to the first buckling preventing member 4 to provide an extra buckling strength about 5 to 10 times as high as that of the flexible sheath 1.

As a result, when the proximal end portion of the flexible sheath 1 is bent with respect to the operating part 10 as shown by the dashed lines in FIG. 1, no sharp bend occurs, and thus buckling breakage of the flexible sheath 1 is prevented.

Figure 3:
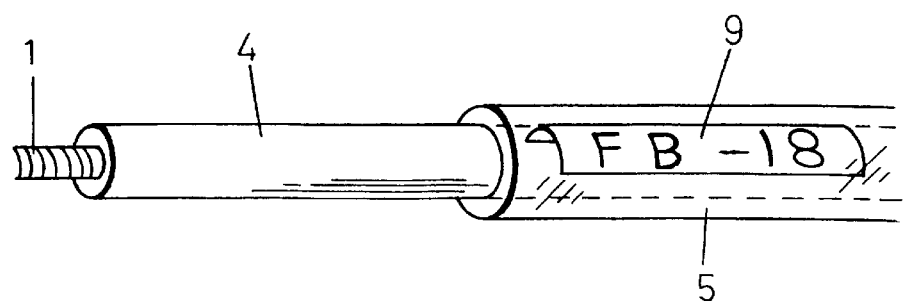
FIG. 3 is a perspective view showing a buckling preventing member part of the treating instrument according to the first embodiment of the present invention.

FIG. 3 is an enlarged view of the first and second buckling preventing members 4 and 5. At a portion where the two buckling preventing members 4 and 5 overlap each other to form a double tube structure, the second buckling preventing member 5, which is placed outside the first buckling preventing member 4, is formed from a transparent or semi-transparent member, and an identification label 9 is sandwiched between the first and second buckling preventing members 4 and 5 to identify the type of the treating instrument and so forth. The identification label 9 is printed with, for example, the model name (e.g. FB-18) of the treating instrument.

If a heat-shrinkable tube (e.g. made of polytetrafluoroethylene, polyethylene, chloroethylene, or et al.) is used as the second buckling preventing member 5, the identification label 9 can be fixed simply by putting it between the first buckling preventing member 4 and the second buckling preventing member 5, without carrying out a bonding process or the like.

Figure 4:
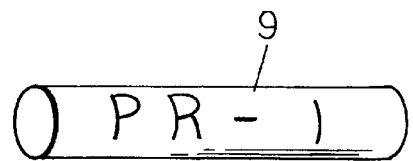
FIG. 4 is a perspective view showing another example of an identification label used for the treating instrument according to the first embodiment of the present invention.

If a colored semitransparent member (e.g. made of polytetrafluoroethylene, polyethylene, chloroethylene, polyurethane or et al. in which pigments are mixed) is used as the second buckling preventing member 5, another identification can be made by the difference in color of the second buckling preventing member 5. The identification label 9 may be formed in a cylindrical shape as shown in FIG. 4.

Figure 5:
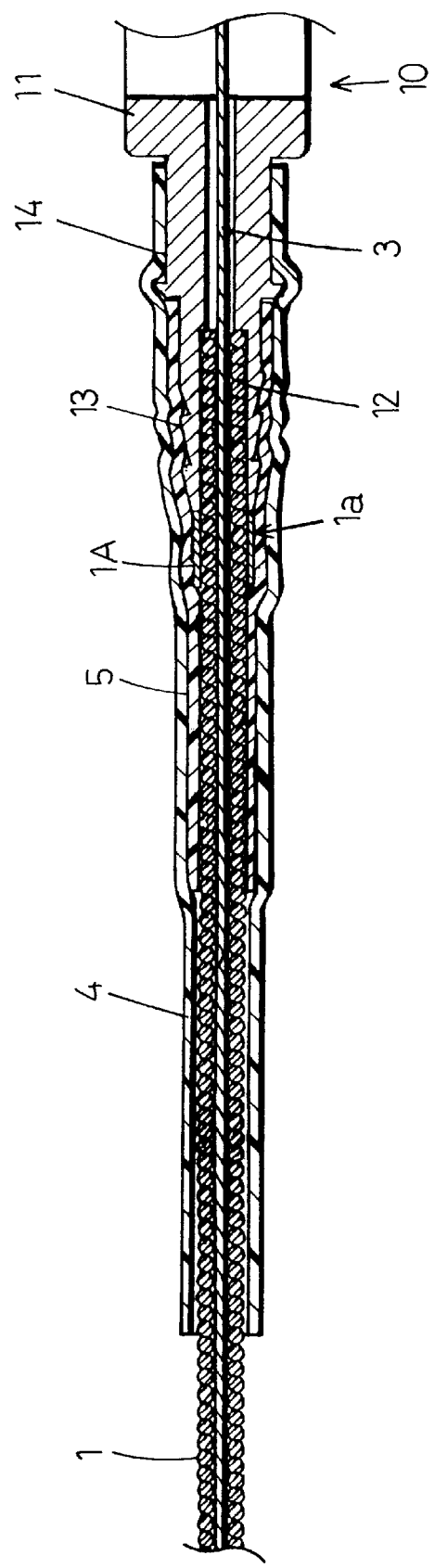
FIG. 5 is a sectional side view of a treating instrument for an endoscope according to a second embodiment of the present invention, showing the joint between a flexible sheath and an operating part and its vicinities.

FIG. 5 is a sectional side view of a treating instrument according to a second embodiment of the present invention, showing the joint between the flexible sheath 1 and the operating part 10 and its vicinities. In the second embodiment, a second buckling preventing member 5 shorter than a first buckling preventing member 4 is placed inside the first buckling preventing member 4. Thus, the flexible sheath 1 is pressed against and thus secured to the operating part body 11 by the second buckling preventing member 5.

The first buckling preventing member 4, which is placed outside the second buckling preventing member 5, is formed from a transparent or semitransparent heat-shrinkable tube, for example. A forward end portion of the first buckling preventing member 4 that does not extend over the second buckling preventing member 5 has a diameter reduced to an extent nearly equal to the diameter of the second buckling preventing member 5. The second embodiment also provides the advantageous effects similar to those obtained by the first embodiment.

Figure 6:
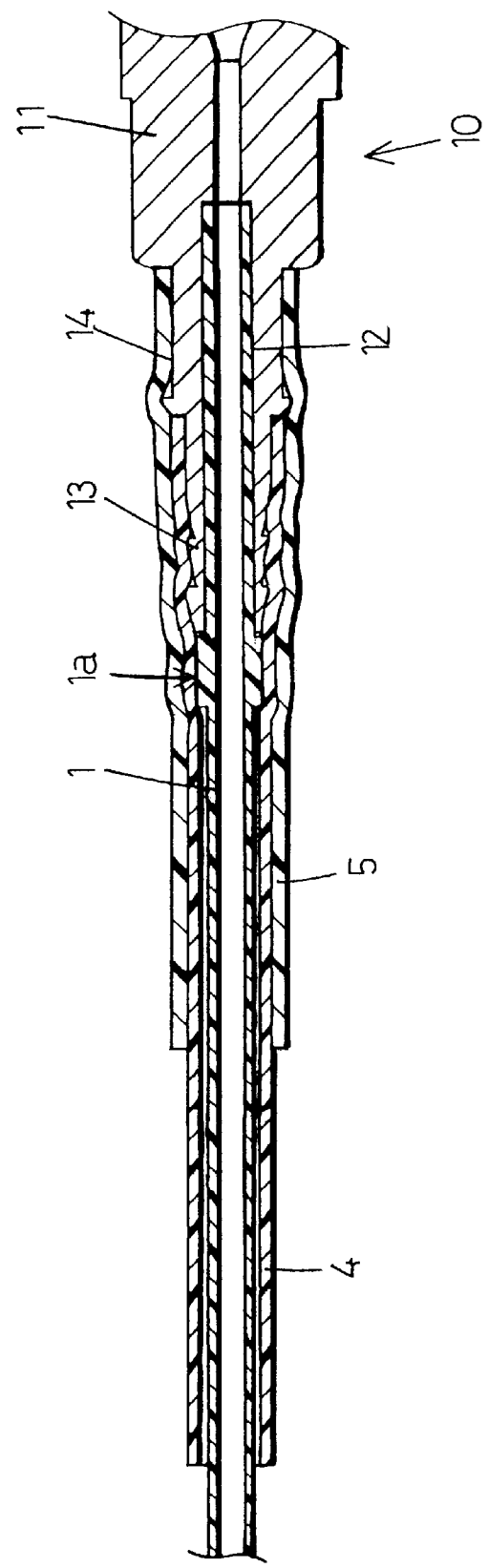
FIG. 6 is a sectional side view of a treating instrument for an endoscope according to a third embodiment of the present invention, showing the joint between a flexible sheath and an operating part and its vicinities.

FIG. 6 shows a third embodiment in which the present invention is applied to a catheter or the like for use with an endoscope in which a flexible sheath 1 is formed from a flexible tube such as a tetrafluoroethylene resin tube. In this embodiment, a large-diameter portion 1a is formed by the flexible sheath 1 itself. However, the arrangement of a first buckling preventing member 4 and a second buckling preventing member 5, which protect the proximal end portion of the flexible sheath 1, and the function and effect thereof are the same as in the first embodiment.

According to the present invention, the proximal end portion of the flexible sheath is covered with the first and second buckling preventing members disposed to overlap each other in such a manner that the first buckling preventing member extends forward beyond the distal end of the second buckling preventing member. Therefore, the buckling strength of the proximal end portion of the flexible sheath can be changed in two steps at a region from the distal end of the first buckling preventing member to the joint between the flexible sheath and the operating part. Consequently, the proximal end portion of the flexible sheath can be bent smoothly without a sharp bend. Thus, buckling breakage of the flexible sheath can be surely prevented.

While the invention has been described by reference to specific embodiments chosen for purposes of illustration, it should be apparent that numerous modifications could be made thereto by those skilled in the art without departing from the basic concept and scope of the invention.

What is claimed is:

1. A treating instrument for an endoscope having a flexible sheath and an operating part connected to a proximal end of said flexible sheath, said treating instrument comprising:
    a first flexible buckling preventing member that covers a proximal end portion of said flexible sheath, one end of said first buckling preventing member being secured to said operating part; and
    a second flexible buckling preventing member that overlaps said first buckling preventing member at an overlap region extending from an intermediate position on said first buckling preventing member to a proximal end thereof, one end of said second buckling preventing member being secured to said operating part,
    wherein at least one of said first buckling preventing member and said second buckling preventing member comprises a heat-shrinkable material.

2. The treating instrument for an endoscope according to claim 1, wherein said first buckling preventing member and said second buckling preventing member each comprises a flexible tube having a uniform wall thickness.

3. The treating instrument for an endoscope according to claim 1, wherein said first buckling preventing member is inside said second buckling preventing member at said overlap region.

4. The treating instrument for an endoscope according to claim 1, wherein said first buckling preventing member is outside said second buckling preventing member at said overlap region, and a portion of said first buckling preventing member that does not extend over said second buckling preventing member has a reduced diameter nearly equal to a diameter of said second buckling preventing member.

5. The treating instrument for an endoscope according to claim 1, wherein said flexible sheath is pressed against and thus secured to said operating part by either one of said first buckling preventing member and said second buckling preventing member that is inside the other at said overlap region.

6. The treating instrument for an endoscope according to claim 1, wherein either one of said first buckling preventing member and said second buckling preventing member that is inside the other at said overlap region is secured to said operating part by force-fitting it in a direction identical with a direction in which said flexible sheath is fitted into said operating part.

7. The treating instrument for an endoscope according to claim 1, wherein, at said overlap region, an identification indicating member is provided between said first buckling preventing member and said second buckling preventing member to identify a type of said treating instrument, and either one of said first buckling preventing member and said second buckling preventing member that is outside the other comprises one of a transparent member and a semitransparent member.

8. The treating instrument for an endoscope according to claim 7, wherein either one of said first buckling preventing member and said second buckling preventing member that is outside the other at said overlap region comprises a colored semitransparent member.

9. A treating instrument for an endoscope having a flexible sheath and an operating part connected to a proximal end of said flexible sheath, said treating instrument comprising:
    a first flexible buckling preventing member that covers a proximal end portion of said flexible sheath, one end of said first buckling preventing member being secured to said operating part; and
    a second flexible buckling preventing member that overlaps said first buckling preventing member at an overlap region extending from an intermediate position on said first buckling preventing member to a proximal end thereof, one end of said second buckling preventing member being secured to said operating part,
    wherein, at said overlap region, an identification indicating member is provided between said first buckling preventing member and said second buckling preventing member to identify a type of said treating instrument, and either one of said first buckling preventing member and said second buckling preventing member that is outside the other comprises one of a transparent member and a semitransparent member.

10. The treating instrument for an endoscope according to claim 9, wherein either one of said first buckling preventing member and said second buckling preventing member that is outside the other at said overlap region comprises a colored semitransparent member.

* * * * *